(12) United States Patent
Puckette

(10) Patent No.: US 8,492,593 B2
(45) Date of Patent: Jul. 23, 2013

(54) AMIDO-FLUOROPHOSPHITE COMPOUNDS AND CATALYSTS

(75) Inventor: Thomas Allen Puckette, Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 73 days.

(21) Appl. No.: 13/210,986

(22) Filed: Aug. 16, 2011

(65) Prior Publication Data
US 2013/0046112 A1 Feb. 21, 2013

(51) Int. Cl.
*C07C 45/50* (2006.01)
*C07C 233/00* (2006.01)
*C07F 9/02* (2006.01)
*C07F 9/26* (2006.01)
*B01J 31/02* (2006.01)

(52) U.S. Cl.
USPC ............. 568/12; 568/15; 568/16; 568/451; 564/161; 558/178; 502/166; 502/167

(58) Field of Classification Search
USPC ............. 568/12, 15, 16, 451, 454; 564/161
See application file for complete search history.

(56) References Cited

U.S. PATENT DOCUMENTS

| | | | |
|---|---|---|---|
| 3,239,566 A | 3/1966 | Slaugh et al. | |
| 3,242,171 A | 3/1966 | Schmutzler | |
| 3,527,809 A | 9/1970 | Pruett et al. | |
| 4,595,753 A | 6/1986 | Oswald et al. | |
| 4,605,781 A | 8/1986 | Tau | |
| 4,608,239 A | 8/1986 | Devon | |
| 4,642,395 A | 2/1987 | Hunter et al. | |
| 4,871,878 A | 10/1989 | Puckette et al. | |
| 5,059,710 A | 10/1991 | Abatjoglou et al. | |
| 5,840,647 A | 11/1998 | Puckette et al. | |
| 6,130,358 A | 10/2000 | Tolleson et al. | |
| 6,664,427 B1 | 12/2003 | Burke et al. | |
| 7,495,133 B2 | 2/2009 | Borgmann et al. | |

OTHER PUBLICATIONS

Cotton, F. Albert and Wilkinson, Geoffrey; "Advanced Inorganic Chemistry, a Comprehensive Text", 3rd Edition, 1972, Wiley and Sons, pp. 374-375.
Edmundson, R. S.; "Dictionary of Organophosphorus Compounds", 1988, Chapman and Hall, pp. 144 and 149, entries C-00063 and C-00092.
Falbe, J.; "New Syntheses with Carbon Monoxide" 1980, Springer-Verlag; pp. 73-77.
Kosolapoff, Gennady M.; "Chapter 8: Phosphites and Thiophosphites" Organophosphorus Compounds, 1950, Wiley and Sons; pp. 180-199.
Notification of Transmittal of the international Search Report and the Written Opinion of the International Searching Authority, or the Declaration date of mailing Nov. 22, 2012 received in the corresponding International Patent Application No. PCT/US2012/049424.

*Primary Examiner* — Sikarl Witherspoon
(74) *Attorney, Agent, or Firm* — Ying Yufan Luo

(57) ABSTRACT

Amido-fluorophosphite compounds and catalyst systems comprising at least one amido-fluorophosphite ligand compound in combination with a transition metal are described. Moreover, the use of amido-fluorophosphite containing catalysts for transition metal catalyzed processes, especially to the hydroformylation of various olefins to produce aldehydes are also described.

18 Claims, No Drawings

AMIDO-FLUOROPHOSPHITE COMPOUNDS AND CATALYSTS

FIELD OF THE INVENTION

This invention relates to amido-fluorophosphite compounds and catalyst systems comprising at least one amido-fluorophosphite ligand compound in combination with a transition metal. The invention also relates to the use of amido-fluorophosphite containing catalysts for transition metal catalyzed processes, especially to the hydroformylation of various olefins to produce aldehydes.

BACKGROUND OF THE INVENTION

The hydroformylation reaction, also known as the oxo reaction, is used extensively in commercial processes for the preparation of aldehydes by the reaction of one mole of an olefin with one mole each of hydrogen and carbon monoxide. The most extensive use of the reaction is in the preparation of normal- and iso-butyraldehyde from propylene. The ratio of the amount of the normal aldehyde product to the amount of the iso aldehyde product typically is referred to as the normal to iso (N:I) or the normal to branched (N:B) ratio. In the case of propylene, the normal- and iso-butyraldehydes obtained from propylene are in turn converted into many commercially-valuable chemical products such as, for example, n-butanol, 2-ethyl-hexanol, n-butyric acid, iso-butanol, neo-pentyl glycol, 2,2,4-trimethyl-1,3-pentanediol, the mono-isobutyrate and di-isobutyrate esters of 2,2,4-trimethyl-1,3-pentanediol. The hydroformylation of higher α-olefins such as 1-octene, 1-hexene and 1-tetradecene yield aldehyde products which are useful feedstocks for the preparation of detergent alcohols and plasticizer alcohols.

A low pressure hydro-formylation process using trialkylphosphines in combination with rhodium catalysts for the preparation of aldehydes has been described. Moreover, trialkylphosphines have seen much use in industrial hydroformylation processes but they typically produce a limited range of products and, furthermore, frequently are very oxygen sensitive. Other methods involve a low pressure hydroformylation process which utilizes triarylphosphine or triarylphosphite ligands in combination with rhodium catalysts. Such ligands, although used in many commercial applications, have limitations due to oxidative and hydrolytic stability problems. Since these early processes, numerous improvements have been made to increase the catalyst stability, catalyst activity and the product ratio with a heavy emphasis on yielding linear aldehyde product. A wide variety of monodentate phosphite and phosphine ligands, bidentate ligands such as bisphosphites and bisphosphines as well as tridentate and polydentate ligands have been prepared and disclosed in the literature.

Once such improvement involved a ligand design which employed halogen substituents on the phosphorus atom of trivalent phosphorus ligands. These halogenated phosphorus ligands are readily prepared and possess high activity, good stability and permit a wide N/I range of products to be prepared by simple variations in the process parameters.

Notwithstanding the substantial progress which has been made in the area of hydroformylation catalyst systems and catalysis in general, there still exists a need to develop more stable, less expensive and more selective catalysts systems with an emphasis on hydroformylation catalysts.

BRIEF SUMMARY OF THE INVENTION

A first embodiment of the present invention concerns a compound having the general structure (I)

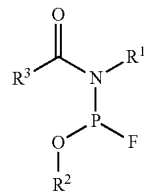

wherein $R^1$, $R^2$, and $R^3$ are hydrocarbyl groups which contain a total of up to about 40 carbon atoms.

Another invention concerns a catalyst comprising:

i. at least one amido-fluorophosphite ester ligand having the general structure (I)

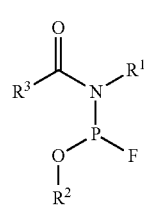

wherein $R^1$, $R^2$, and $R^3$ are hydrocarbyl groups which contain a total of up to about 40 carbon atoms, ii. at least one transition metal; and iii. a solvent.

Yet another embodiment concerns a process for preparing an amido-fluorophosphite ester ligand comprising contacting an amido-chlorophosphite and a fluoride containing compound in a solvent to produce the amido-fluorophosphite compound.

Still another embodiment concerns a process for the production of an aldehyde comprising contacting hydrogen, carbon monoxide, and an olefin in the presence of a catalyst comprising:

i. at least one amido-fluorophosphite ester ligand having the general structure (I)

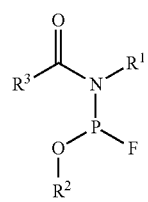

wherein $R^1$, $R^2$, and $R^3$ are hydrocarbyl groups which contain a total of up to about 40 carbon atoms, ii. at least one transition metal, and iii. a solvent.

DETAILED DESCRIPTION

According to an embodiment, the present invention concerns amido-fluorophosphite ester compounds having the general structure (I)

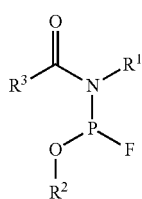

(I)

wherein $R^1$, $R^2$, and $R^3$ are hydrocarbyl groups which contain a total of up to about 40 carbon atoms. This class of compounds is useful as ligands in transition metal catalyzed reactions. The amido-fluorophosphite ester compounds (or ligands) of the present invention can be substituted for, or used in combination with, known phosphite and/or phosphine ligands in a wide variety of catalyst systems using a transition metal as the primary catalyst component.

Another embodiment concerns a catalyst system comprising a combination of one or more transition metals, especially those selected from the Group VIII metals, and one or more amido-fluorophosphite ester ligands having the general formula (I) wherein $R^1$, $R^2$, and $R^3$ are hydrocarbyl groups which contain a total of up to about 40 carbon atoms and wherein the ratio of gram moles amido-fluorophosphite ester ligands to gram atoms transition metal is from about 1:1 to about 300:1; from about 2:1 to about 150:1, or from about 10:1 to about 75:1. The catalyst systems may be used in a wide variety of transition metal-catalyzed processes such as, for example, hydroformylation, hydrogenation, isomerization, hydrocyanation, hydrosilation, carbonylations, oxidations, acetoxylations, epoxidations, hydroamination, dihydroxylation, cyclopropanation, telomerizatons, carbon hydrogen bond activation, olefin metathesis, olefin dimerizations, oligomerizations, olefin polymerizations, olefin-carbon monoxide copolymerizations, butadiene dimerization and oligomerization, butadiene polymerization, and other carbon-carbon bond forming reactions such as the Heck reaction and arene coupling reactions. The catalyst systems comprising rhodium as the transition metal are useful, for example, for the hydroformylation of olefins to produce aldehydes.

Another embodiment concerns a catalyst solution comprising (1) one or more of the amido-fluorophosphite ester ligands of formula (I), (2) rhodium, and (3) a hydroformylation solvent. This embodiment comprises a solution of the active catalyst in which a carbonylation process such as the hydroformylation of an ethylenically-unsaturated compound may be carried out.

Another embodiment concerns a hydroformylation process utilizing the above-described catalyst systems and solutions. The process of the present invention therefore includes a process for preparing an aldehyde which comprises contacting an olefin, hydrogen and carbon monoxide with a solution of a catalyst system comprising rhodium and an amido-fluorophosphite ligand of formula (I) wherein the mole ratio of phosphorus ligand:rhodium is from about 1:1 to about 300:1; from about 2:1 to about 150:1, or from about 10:1 to about 75:1.

According to present invention, the amido-fluorophosphite ester ligands may contain one, two, or more trivalent phosphorus centers which are capable of forming complexes with transition metals. These ligands are often referred to as monodentate, bidentate, and polydentate ligands. The ligand compounds contemplated in this invention may contain one, two, or more amido-fluorophosphite groups and form monodentate, bidentate and polydentate complexes with transition metals.

It is generally recognized in the art that the presence of halogens in hydroformylation catalysts normally reduces substantially the activity of the catalyst. Moreover, the literature contains numerous references and citations where halogens are identified as poisons in the rhodium catalyzed hydroformylation process. For example, Falbe ("New Syntheses with Carbon Monoxide" edited by J. Falbe, 1980, Springer-Verlag) on page 73 lists halogens as poisons for hydroformylation catalysts. U.S. Pat. Nos. 5,059,710, 4,595,753, 4,605,781 and 4,642,395 teach that halogen atoms generally are detrimental to the activity of hydroformylation catalyst systems. U.S. Pat. No. 4,871,878 discloses that halogens may be present in the organic structure of a ligand, but these halogen-containing substituents typically have the halogen located in a stable, non-hydrolyzable group, away from the phosphorus center and sufficiently far removed from the rhodium atom that no interactions can occur. For example, U.S. Pat. No. 4,871,878 teaches the use of halogen substituted tribenzylphosphine ligands except those cases where the chlorine, bromine or iodine are in the positions adjacent to the benzylic group.

Reactions of halophosphorus compounds with hydroxylic materials or water are well known in the chemical literature. Cotton and Wilkinson ("Advanced Inorganic Chemistry", 3rd Edition, 1972, Wiley and Sons, pages 374-375) describe the phosphorus halides as materials that are hydrolyzed, sometimes violently, in the presence of water. Kosolapoff reported many years ago ("Organophosphorus Compounds", 1950, Wiley and Sons, pages 180 to 199) that the halophosphites are unstable to heat, and react with water, alcohols, and phenols. Chlorophosphites have been characterized as "Rapidly hydrolyzed" and "Reacts violently with water" ("Dictionary Of Organo-phosphorus Compounds", edited by Edmundson, 1988, Chapman and Hall, pages 144 and 149, entries C-00063 and C-00092). The reactions with the hydroxylic materials generate phosphoric acid esters as the initial product and hydrogen halides. Hydrogen halides have been described as poisons to many transition metal-catalyzed processes such as the hydroformylation reaction. Therefore, the presence of any phosphorus halide species in a hydroformylation reaction usually is deemed undesirable.

Contrary to the teachings of the art discussed above, we have found that the amido-fluorophosphite ester compounds having the formula

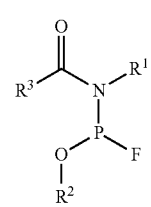

(I)

function as effective ligands when used in combination with transition metals to form catalyst systems for the processes described hereinabove. The hydrocarbyl groups represented by $R^1$, $R^2$, and $R^3$ may be the same or different, separate or combined, and are selected from unsubstituted and substituted alkyl, cycloalkyl and aryl groups containing a total of up to about 40 carbon atoms. The total carbon content of substituents $R^1$, $R^2$, and $R^3$ preferably is in the range of about 3 to 70 carbon atoms. Examples of the alkyl groups which $R^1$ and/or $R^2$ and/or $R^3$ separately or individually can represent include methyl, ethyl, butyl, pentyl, hexyl, 2-ethylhexyl, octyl, decyl, dodecyl, octadecyl and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. Cyclopentyl, cyclohexyl and cycloheptyl are examples of the cycloalkyl groups $R^1$ and/or $R^2$ and/or $R^3$ individually can represent. The cycloalkyl groups may be substituted with alkyl or any of the substituents described with respect to the possible substituted alkyl groups. The alkyl and cycloalkyl groups which $R^1$, $R^2$, and $R^3$ individually can represent can be alkyl of up to about 8 carbon atoms, such as benzyl, cyclopentyl, cyclohexyl or cycloheptyl.

Examples of the aryl groups which $R^1$, and/or $R^2$, and/or $R^3$ individually can represent carbocyclic aryl such as phenyl, naphthyl, anthracenyl and substituted derivatives thereof. Examples of the carbocyclic aryl groups which $R^1$, and/or $R^2$, and/or $R^3$ individually can represent the groups having the formulas

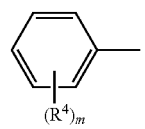
(II)

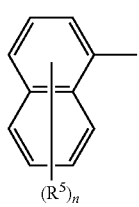
(III)

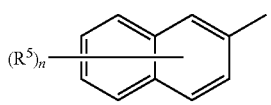
(IV)

wherein $R^4$ and $R^5$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms. Although it is possible for m to represent 0 to 5 and for n to represent 0 to 7, the value of each of m and n usually will not exceed 2. $R^4$ and $R^5$ can represent lower alkyl groups, i.e., straight-chain and branched-chain alkyl of up to about 8 carbon atoms, and m and n each represent 0, 1 or 2.

Alternatively, $R^2$ and $R^3$ in combination or collectively may represent a divalent hydrocarbylene group containing up to about 40 carbon atoms, for example, from about 6 to 36 carbon atoms. Examples of such divalent groups include alkylene of about 2 to 12 carbon atoms, cyclohexylene and arylene. Specific examples of the alkylene and cycloalkylene groups include ethylene, trimethylene, 1,3-butanediyl, 2,2-dimethyl-1,3-propanediyl, 1,1,2-triphenylethanediyl, 2,2,4-trimethyl-1,3-pentanediyl, 1,2-cyclohexylene, and the like.

Examples of the arylene groups which $R^2$ and $R^3$ collectively may represent are given hereinbelow as formulas (V), (VI) and (VII).

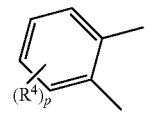
(V)

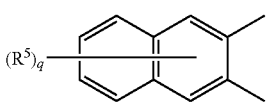
(VI)

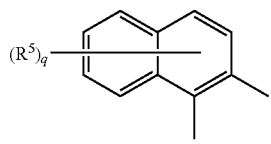
(VII)

wherein $R^4$ and $R^5$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of such alkyl, alkoxy, alkanoyl, alkoxycarbonyl and alkanoyloxy groups typically contains up to about 8 carbon atoms. Although it is possible for p to represent 0 to 4 and for q to represent 0 to 6, the value of each of p and q usually will not exceed 2. $R^4$ and $R^5$ may represent lower alkyl groups, i.e., straight-chain and branched-chain alkyl of up to about 4 carbon atoms, and p and q each represent 0, 1 or 2.

The divalent groups that $R^2$ and $R^3$ collectively may represent include groups having the formula

wherein each of $A^1$ and $A^2$ is an arylene radical, e.g., a divalent, carbocyclic aromatic group containing 6 to 10 ring carbon atoms, wherein the ester oxygen atom of the amido-fluorophosphite (I) is bonded to a ring carbon atom of either $A^1$ or $A^2$ and the carboxamide group of the amido-fluorophosphite is bonded to the remaining carbocyclic aromatic group.

X is (i) a chemical bond directly between ring carbon atoms of $A^1$ and $A^2$ or (ii) an oxygen atom, a group having the formula —$(CH_2)_y$— wherein y is 2 to 4 or (iii) a group having the formula

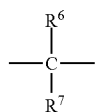

wherein $R^6$ is hydrogen, alkyl or aryl, e.g., the aryl groups illustrated by formulas (II), (III) and (IV), and $R^7$ is hydrogen or alkyl. The total carbon content of the group —$C(R^6)(R^7)$— normally will not exceed 20 and can be in the range of 1 to 8 carbon atoms.

Examples of the arylene groups represented by each of $A^1$ and $A^2$ include the divalent groups having the formulas:

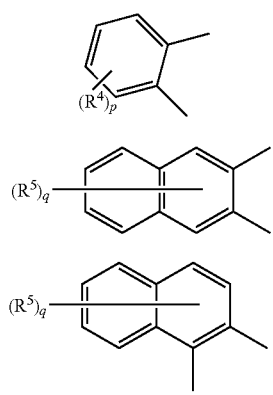

(V)

(VI)

(VII)

wherein $R^4$ and $R^5$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts and the like. The alkyl moiety of such alkyl, alkoxy, alkanoyl, alkoxycarbonyl and alkanoyloxy groups typically contains up to about 8 carbon atoms. Although it is possible for p to represent 0 to 4 and for q to represent 0 to 6, the value of each of p and q usually will not exceed 2. $R^4$ and $R^5$ may represent lower alkyl groups, i.e., straight-chain and branched-chain alkyl of up to about 4 carbon atoms, and p and q each represent 0, 1 or 2.

The amido-fluorophosphite ester compounds can include those esters wherein the amido-fluorophosphite ester oxygen atom is bonded directly to a ring carbon atom of a carbocyclic, aromatic group, e.g., an aryl or arylene group represented by any of formulas (II) through (VII) and the acyl group of amido group is bonded to the same carbocyclic aromatic group. The ester oxygen and the amido acyl group may be bonded to adjacent carbon atoms of the carbocyclic aromatic group which results in a six member ring amido-fluoro phosphite such as compound (VIII).

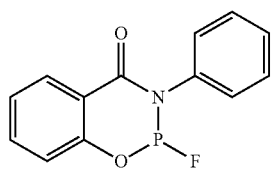 [SMILES: O=C1c2ccccc2OP(F)N1c1ccccc1]

(VIII)

Another embodiment concerns a process for preparing an amido-fluorophosphite ester compound comprising contacting an amido-chlorophosphite and a fluoride containing compound in a solvent to produce the amido-fluorophosphite compound. The amido-fluorophosphite esters of formula (I) may be prepared from the corresponding amido-chlorophosphites. The preparation of the amido-chlorophosphites has been previously described in U.S. Pat. No. 7,495,133, example 18 and is U.S. Pat. No. 6,664,427, example 1. Both of these patents teach the reaction of salicylanilide with phosphorus trichloride but under differing reaction conditions. Moreover, the introduction of the fluoride compound can be accomplished by many different reagents, for example, anhydrous hydrogen fluoride, hydrogen fluoride-pyridine complex, potassium fluoride, ammonium fluoride, antimony trifluoride in combination with triethyl amine, or cesium fluoride.

The organic moiety of the amido-fluorophosphite compounds, i.e., the residue(s) represented by $R^1$, $R^2$, and $R^3$ can be derived from chiral or optically active compounds.

Amido-fluorophosphite ester ligands derived from chiral amines or chiral phenols will generate chiral ligands. Ligands consisting of the chiral amido-fluorophosphites can be used in many transition metal catalyzed processes including, but not limited to, hydroformylation, hydrogenation, hydrocyanation, hydrosilation, carbonylations, oxidations, acetoxylations, epoxidations, hydroamination, dihydroxylation, cyclopropanation, carbon hydrogen bond activation, olefin metathesis, olefin dimerizations, olefin oligomerizations, olefin polymerizations, olefin-carbon monoxide copolymerizations, butadiene dimerization and oligomerization, butadiene polymerization, and other carbon-carbon bond forming reactions such as the Heck reaction to yield enantioselective product mixtures.

According to an embodiment, the catalyst systems provided by the present invention comprise a combination of one or more transition metals, such as those selected from the Group VIII metals, and one or more of the amido-fluorophosphite compounds described in detail hereinabove. The transition metal may be provided in the form of various metal compounds such as carboxylate salts of the transition metal. Rhodium compounds that may be used as a source of rhodium for the active catalyst include rhodium (II) or rhodium (III) salts of carboxylic acids, examples of which include di-rhodium tetraacetate dihydrate, rhodium(II) acetate, rhodium(II) isobutyrate, rhodium(II) 2-ethylhexanoate, rhodium (II) benzoate and rhodium(II) octanoate. Also, rhodium carbonyl species such as $Rh_4(CO)_{12}$, $Rh_6(CO)_{16}$ and rhodium(I) acetylacetonate dicarbonyl may be suitable rhodium feeds. Additionally, rhodium organophosphine complexes such as tris(triphenylphosphine) rhodium carbonyl hydride may be used when the phosphine moieties of the complex fed are easily displaced by the amido-fluorophosphite ligands of the present invention. Less desirable rhodium sources are rhodium salts of strong mineral acids such as chlorides, bromides, nitrates, sulfates, phosphates and the like.

The ratio of gram moles amido-fluorophosphite ester ligand to gram atoms transition metal can vary over a wide range, e.g., gram mole amido-fluorophosphite:gram atom transition metal ratios of from about 1:1 to about 300:1; from about 2:1 to about 150:1, or from about 10:1 to about 75:1. For the rhodium-containing catalyst systems, the gram mole amido-fluorophosphite:gram atom rhodium ratio can be in the range of about 1:1 up to 300:1 such as ratios in the range of about 1:1 to 75:1.

Another embodiment concerns a catalyst solution comprising (1) one or more of the amido-fluorophosphite ester ligands of formula (I), (2) rhodium and (3) a hydroformylation solvent. This embodiment comprises a solution of the active catalyst in which a carbonylation process such as the hydroformylation of an ethylenically-unsaturated compound may be carried out.

The hydroformylation reaction solvent may be selected from a wide variety of compounds, mixture of compounds, or materials that are liquid at the pressure at which the process is being operated. Such compounds and materials include various alkanes, cycloalkanes, alkenes, cycloalkenes, carbocyclic aromatic compounds, alcohols, esters, ketones, acetals, ethers and water. Specific examples of such solvents include alkane and cycloalkanes such as dodecane, decalin, octane, iso-octane mixtures, cyclohexane, cyclooctane, cyclododecane, methylcyclohexane; aromatic hydrocarbons such as benzene, toluene, xylene isomers, tetralin, cumene, alkyl-substituted aromatic compounds such as the isomers of diisopropylbenzene, triisopropylbenzene and tert-butylbenzene; alkenes and cycloalkenes such as 1,7-octadiene, dicyclopentadiene, 1,5-cyclooctadiene, octene-1, octene-2,4-vinylcyclohexene, cyclohexene, 1,5,9-cyclododecatriene, 1-pentene; crude hydrocarbon mixtures such as naphtha, mineral oils and kerosene; high-boiling esters such as 2,2,4-trimethyl-1,3-pentanediol diisobutyrate. The aldehyde product of the hydroformylation process also may be used. In practice, the solvent can be the higher boiling by-products that are naturally formed during the process of the hydroformylation reaction and the subsequent steps, e.g., distillations, that are required for aldehyde product isolation. A criterion for the solvent is that it dissolves the catalyst and olefin substrate and does not act as a poison to the catalyst. Such solvents for the production of volatile aldehydes, e.g., propionaldehyde and the butyraldehydes, include those that are sufficiently high boiling to remain, for the most part, in a gas sparged reactor. Solvents and solvent combinations that can be used in the production of less volatile and non-volatile aldehyde products include 1-methyl-2-pyrrolidinone, dimethyl-formamide, perfluorinated solvents such as perfluoro-kerosene, sulfolane, water, and high boiling hydrocarbon liquids as well as combinations of these solvents. Non-hydroxylic compounds, in general, and hydrocarbons, in particular, may be used as the hydroformylation solvent since their use can minimize decomposition of the amido-fluorophosphite ester ligands.

The concentration of the rhodium and ligand in the hydroformylation solvent or reaction mixture is not critical for the successful operation of the invention. As mentioned hereinabove, a gram mole ligand:gram atom rhodium ratio of at least 1:1 normally is maintained in the reaction mixture. The absolute concentration of rhodium in the reaction mixture or solution may vary from 1 mg/liter up to 5000 mg/liter or more. When the process is operated within the practical conditions of this invention, the concentration of rhodium in the reaction solution normally is in the range of about 20 to 300 mg/liter. Concentrations of rhodium lower than this range generally do not yield acceptable reaction rates with most olefin reactants and/or require reactor operating temperatures that are so high as to be detrimental to catalyst stability. Higher rhodium concentrations are not preferred because of the high cost of rhodium.

No special or unusual techniques are required for preparing the catalyst systems and solutions of the present invention. However, to obtain a catalyst of high activity, all manipulations of the rhodium and amido-fluorophosphite ligand components can be carried out under an inert atmosphere, e.g., nitrogen, argon and the like. The desired quantities of a suitable rhodium compound and ligand are charged to the reactor in a suitable solvent. The sequence in which the various catalyst components or reactants are charged to the reactor is not critical.

Another embodiment pertains to a hydroformylation process utilizing the above-described catalyst systems and solutions. The process of the present invention therefore is a process for preparing an aldehyde which comprises contacting an olefin, hydrogen and carbon monoxide with a solution of a catalyst system comprising rhodium and an amido-fluorophosphite ligand of formula (I) wherein the ratio of gram moles ligand:gram atom rhodium is from about 1:1 to about 300:1; from about 2:1 to about 150:1, or from about 10:1 to about 75:1.

The olefins that may be hydroformylated by means of the process comprise aliphatic, including ethylenically-unsaturated, low molecular weight polymers, alicyclic, aromatic and heterocyclic mono-, di- and tri-olefins containing up to about 40 carbon atoms. Examples of the aliphatic olefins that may be utilized in the process include straight- and branched-chain, unsubstituted and substituted, aliphatic mono α-olefins and internal olefins containing up to about 20 carbon atoms. Examples of the groups that may be present on the substituted mono α-olefins include hydroxy; alkoxy including ethers and acetals; alkanoyloxy such as acetoxy; amino including substituted amino; carboxy; alkoxycarbonyl; carboxamido; keto; cyano; and the like. Preferred aliphatic mono α-olefins have the general formulas:

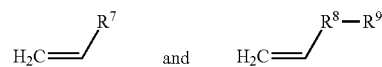

wherein $R^7$ is hydrogen or straight- or branched-chain alkyl of up to about 40 carbon atoms, or $R^7$ may be an oxygen atom which is part of a larger group such as a carboxylate or ether linkage;

$R^8$ is straight- or branched-chain alkylene of up to about 18 carbon atoms; and $R^9$ is hydroxy, alkoxy of up to about 4 carbon atoms, alkanoyloxy of up to about 4 carbon atoms, carboxyl or alkoxycarbonyl of 2 to about 10 carbon atoms.

Specific examples of the aliphatic mono α-olefins include ethylene, propylene, 1-butene, 1-octene, vinyl acetate, vinyl isobutyl ether, allyl alcohol and 3-acetoxy-1-propene.

The aliphatic, di-olefins may contain up to about 40 carbon atoms. Examples of the aliphatic, di-olefins have the general formula:

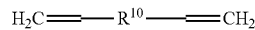

wherein $R^{10}$ is straight- or branched-chain alkylene having 1 to about 18 carbon atoms.

Internal olefins can also be used in the hydroformylation process. Examples of internal olefins include 2-butene, 2-hexene, 3-hexene and the like.

The cyclic olefins which may be used in the hydroformylation process of the present invention may be cycloalkenes, e.g., cyclohexene, 1,5-cyclooctadiene, and cyclodecatriene, and from various vinyl-substituted cycloalkanes, cycloalkenes, heterocyclic and aromatic compounds. Examples of such cyclic olefins include 4-vinylcyclohexene, 1,3-cyclohexadiene, 4-cyclohexene-carboxylic acid, methyl 4-cyclohexene-carboxylic acid, 1,4-cyclooctadiene and 1,5,9-cyclododecatriene. For example olefin reactants can comprise mono alpha olefins of 2 to 10 carbon atoms, especially propylene. Cyclic olefins and internal olefins are sometimes less reactive that α-olefins but the lower reactivity can be overcome by adjusting process variables such as the reaction temperature or the ligand to rhodium ratio.

Mixtures of olefins can also be used in the practice of this invention. The mixtures may be of the same carbon number such as mixtures of n-octenes or it may represent refinery distillation cuts which will contain a mixture of olefins over a range of several carbon numbers.

The reaction conditions used are not critical for the operation of the process and conventional hydroformylation conditions normally are used. According to an embodiment, an olefin is contacted with hydrogen and carbon monoxide in the presence of the catalyst system described hereinabove. The process may be carried out at temperatures in the range of about 20° to 200° C., from 50° to 135° C. or from 75° to 125° C. Higher reactor temperatures are not favored because of increased rates of catalyst decomposition while lower reactor temperatures result in relatively slow reaction rates. The total reaction pressure may range from about ambient or atmospheric up to 70 bars absolute (about 1000 psig), or from about 8 to 28 bars absolute (about 100 to 400 psig).

The hydrogen:carbon monoxide mole ratio in the reactor likewise may vary considerably ranging from 10:1 to 1:10 and the sum of the absolute partial pressures of hydrogen and carbon monoxide may range from 0.3 to 36 bars absolute. The partial pressures or the ratio of the hydrogen to carbon monoxide in the feed is selected according to the linear:branched isomer ratio desired. Generally, the partial pressure of hydrogen and carbon monoxide in the reactor is maintained within the range of about 1.4 to 13.8 bars absolute (about 20 to 200 psia) for each gas. The partial pressure of carbon monoxide in the reactor is maintained within the range of about 1.4 to 13.8 bars absolute (about 20 to 200 psia) and is varied independently of the hydrogen partial pressure. The molar ratio of hydrogen to carbon monoxide can be varied widely within these partial pressure ranges for the hydrogen and carbon monoxide. The ratios of the hydrogen to carbon monoxide and the partial pressure of each in the synthesis gas (syngas—carbon monoxide and hydrogen) can be readily changed by the addition of either hydrogen or carbon monoxide to the syngas stream. With the amido-fluorophosphite ligands described herein, the ratio of linear to branched products can be varied widely by changing the partial pressures of the carbon monoxide in the reactor.

The amount of olefin present in the reaction mixture also is not critical. For example, relatively high-boiling olefins such as 1-octene may function both as the olefin reactant and the process solvent. In the hydroformylation of a gaseous olefin feedstock such as propylene, the partial pressures in the vapor space in the reactor typically are in the range of about 0.07 to 35 bars absolute. In practice the rate of reaction is favored by high concentrations of olefin in the reactor. In the hydroformylation of propylene, the partial pressure of propylene may be greater than 1.4 bars, e.g., from about 1.4 to 10 bars absolute. In the case of ethylene hydroformylation, the partial pressure of ethylene in the reactor is greater than 0.14 bars absolute.

Any of the known hydroformylation reactor designs or configurations may be used in carrying out the process provided by the present invention. Thus, a gas-sparged, vapor take-off reactor design as disclosed in the examples set forth herein may be used. In this mode of operation, the catalyst which is dissolved in a high boiling organic solvent under pressure does not leave the reaction zone with the aldehyde product taken overhead by the unreacted gases. The overhead gases then are chilled in a vapor/liquid separator to condense the aldehyde product and the gases can be recycled to the reactor. The liquid product is let down to atmospheric pressure for separation and purification by conventional techniques. The process also may be practiced in a batchwise manner by contacting the olefin, hydrogen and carbon monoxide with the present catalyst in an autoclave.

A reactor design where catalyst and feedstock are pumped into a reactor and allowed to overflow with product aldehyde, i.e. liquid overflow reactor design, is also suitable. For example, high boiling aldehyde products such as nonyl aldehydes may be prepared in a continuous manner with the aldehyde product being removed from the reactor zone as a liquid in combination with the catalyst. The aldehyde product may be separated from the catalyst by conventional means such as by distillation or extraction and the catalyst then recycled back to the reactor. Water soluble aldehyde products can be separated from the catalyst by extraction techniques. A trickle-bed reactor design also is suitable for this process. It will be apparent to those skilled in the art that other reactor schemes may be used with this invention.

EXAMPLES

The various embodiments of the present invention are further illustrated by the following examples.

Typical Ligand Preparation

Preparation of 2-fluoro-3-phenyl-2H-benzo[e][1,3,2] oxaza phosphinin-4(3H)-one (Compound VIII). Salicylanilide (26.7 grams, 125 mmole), toluene (600 milliliters), and tetrabutyl ammonium bromide (~0.2 grams) were combined under $N_2$ in a 2 liter three neck flask equipped with a mechanical stirrer, reflux condenser, a rubber septum stoppered inlet, and a Dean-Stark trap. The mixture was heated to reflux to dry the solution by azeotropic distillation. About 75 milliliters of liquid was distilled out to dry the contents of the flask. The equipment was cooled to a safe handling temperature, the Dean Stark trap removed, and any moisture droplets were wiped out of the condenser. Phosphorus trichloride (18.04 grams, 131.3 mmole) was added to the reaction via syringe through the rubber septum. The mixture was stirred and heated to reflux for 0.5 hour. The reaction was allowed to cool to a safe temperature and then rigged for simple distillation. 150 Milliliters of solvent was distilled out to remove the excess $PCl_3$. The glassware was allowed to cool to a safe handling temperature and then ammonium fluoride (5.78 grams, 156.3 mmole) was added to the reaction. The mixture was heated to an internal temperature of 105° C. overnight and checked for completion by GC. Ammonium chloride may sublime out onto the cooler parts of the glassware. Additional $NH_4F$ may be added if needed to drive the reaction to completion. Upon completion, the reaction was cooled to ambient, the solids were filtered out as the reaction contents were passed through a short bed of alumina and the solvent stripped off to afford the crude product as a crystalline mass. The crude material was triturated in an ether/hexane mixture to give the product. The initial product isolated was 21.71 grams of slightly yellow crystals. A second crop was taken by concentration of the liquor and yielded 7.5 grams. $^{31}P$ NMR shows no unreacted chloro-amidophosphite remains and the product gives a doublet centered at 118.5 ppm and coupling constant of 1260 Hertz. The $^1H$ NMR shows a doublet 7.18 ppm (1H), J=8.30 Hz; a doublet of doublets at 8.1 (1H), J=7.81 and 1.71 Hz; and a complex multiplet at 7.25-7.62 (7H).

Hydroformylation Process Set-Up

The hydroformylation process in which propylene is allowed to react with hydrogen and carbon monoxide to produce butyraldehydes was carried out in a vapor take-off reactor made up of a vertically arranged stainless steel pipe having a 2.5 cm inside diameter and a length of 1.2 meters. The reactor was encased in an external jacket that was connected to a hot oil machine. The reactor had a filter element welded into the side near the bottom of the reactor for the inlet of gaseous reactants. The reactor contained a thermocouple which was arranged axially with the reactor in its center for accurate measurement of the temperature of the hydroformylation reaction mixture. The bottom of the reactor had a high pressure tubing connection that was connected to a cross. One of the connections to the cross permitted the addition of non-gaseous reactants such as higher boiling alkenes or make-up solvents, another led to the high-pressure connection of a differential pressure (D/P) cell that was used to measure catalyst level in the reactor and the bottom connection was used for draining the catalyst solution at the end of the run.

In the hydroformylation of propylene in a vapor take-off mode of operation, the hydroformylation reaction mixture or solution containing the catalyst was sparged under pressure with the incoming reactants of propylene, hydrogen and carbon monoxide as well as any inert feed such as nitrogen. As butyraldehyde was formed in the catalyst solution, it and unreacted reactant gases were removed as a vapor from the top of the reactor by a side-port. The vapor removed was chilled in a high-pressure separator where the butyraldehyde product was condensed along with some of the unreacted propylene. The uncondensed gases were let down to atmospheric pressure via the pressure control valve. These gases passed through a series of dry-ice traps where any other aldehyde product was collected. The product from the high-pressure separator was combined with that of the traps, and was subsequently weighed and analyzed by standard gas/liquid phase chromatography (GC/LC) techniques for the net weight and normal/iso ratio of the butyraldehyde product. Activity was calculated as kilograms of butyraldehydes produced per gram of rhodium per hour.

The gaseous feeds to the reactor were fed to the reactor via twin cylinder manifolds and high-pressure regulators. The hydrogen passed through a mass flow controller and then through a commercially available "Deoxo" (registered trademark of Engelhard Inc.) catalyst bed to remove any oxygen contamination. The carbon monoxide passed through an iron carbonyl removal bed (as disclosed in U.S. Pat. No. 4,608,239), a similar "Deoxo" bed heated to 125° C., and then a mass flow controller. Nitrogen can be added to the feed mixture as an inert gas. Nitrogen, when added, was metered in and then mixed with the hydrogen feed prior to the hydrogen Deoxo bed. Propylene was fed to the reactor from feed tanks that were pressurized with hydrogen and was controlled using a liquid mass flow meter. All gases and propylene were passed through a preheater to ensure complete vaporization of the liquid propylene prior to entering the reactor.

The hydroformylation of a higher-boiling, liquid olefin, such as 1-octene, was carried out in a high pressure autoclave. The olefin, catalyst, and solvent were sealed in the autoclave under nitrogen. The reaction mixture was then pressurized with hydrogen and carbon monoxide and heated to the desired reaction temperature. The autoclave was maintained at reaction temperature and pressure selected for a predetermined amount of time or until gas uptake ceased. The autoclave was then cooled to ambient temperature and vented. The contents of the autoclave were recovered and analyzed for olefin and aldehyde content by conventional gas chromatography.

Autoclave Procedure

The following procedure was used for hydroformylation runs in the 300 milliliter Autoclave Engineer autoclaves. A catalyst solution was prepared under nitrogen using a charge of 20 mg of rhodium (0.194 mmol, as rhodium dicarbonyl acetonyl acetate), various amounts of the ligand as indicated in Table 1; 130 ml of Texanol™ Isobutyrate (2,2,4-trimethylpentane-1,3-diol diisobutyrate) and 7.89 grams of 1-octene. The autoclave was sealed under a slight positive pressure of $N_2$, and then was connected to gas feed lines and coolant supply to the internal cooling coil. The autoclave was pressurized to 350 psig with a mixture of hydrogen and carbon monoxide of the ratio specified in the table. The autoclave was heated to the specified temperature and maintained at that temperature for the duration of the run (2 to 3 hours). The syn gas pressure in the autoclave was maintained at 350 psig with make up gas of a 1:1 molar ratio. At the end of the desired run time, the autoclave was cooled, excess gas vented off, and the contents of the autoclave analyzed by gas chromatography.

TABLE I

Hydroformylation of 1-Octene

| | Olefin | Grams olefin | Ligand | Mmole ligand | T° C. | Rh, mg | $H_2$/CO ratio | % conv | N/I |
|---|---|---|---|---|---|---|---|---|---|
| 1 | 1-Octene | 7.89 | 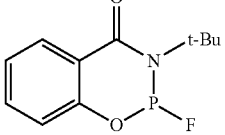 | 1.16 | 95 | 20 | 1 | 51.1 | 0.41 |
| 2 | 1-Octene | 7.89 | 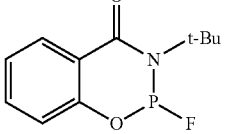 | 2.32 | 95 | 20 | 1 | 41.9 | 0.45 |
| 3 | 1-Octene | 7.89 | 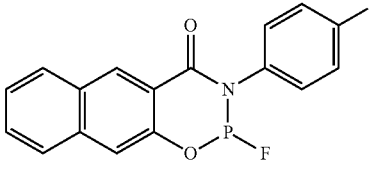 | 2.32 | 95 | 20 | 1 | 73.9 | 3.98 |
| 4 | 1-Octene | 7.89 | 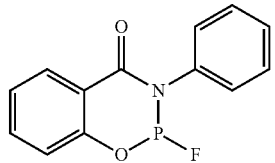 [SMILES: O=C1c2ccccc2OP(F)N1c1ccccc1] | 2.32 | 95 | 20 | 1 | 93.6 | 2.09 |

TABLE I-continued

Hydroformylation of 1-Octene

| | Olefin | Grams olefin | Ligand | Mmole ligand | T° C. | Rh, mg | H$_2$/CO ratio | % conv | N/I |
|---|---|---|---|---|---|---|---|---|---|
| 5 | 1-Octene | 7.89 | *benzoxazaphosphorine-F, N-phenyl* | 4.64 | 95 | 20 | 1 | 83.8 | 3.07 |
| 6 | 1-Octene | 7.89 | *benzoxazaphosphorine-F, N-phenyl* | 6.96 | 95 | 20 | 1 | 76.9 | 4.28 |
| 7 | 1-Octene | 7.89 | *benzoxazaphosphorine-F, N-phenyl* | 11.64 | 95 | 20 | 1 | 79.7 | 6.35 |
| 8 | 1-Octene | 7.89 | *benzoxazaphosphorine-F, N-phenyl* | 6.96 | 95 | 20 | 2 | 76.4 | 7.67 |
| 9 | 1-Octene | 7.89 | *benzoxazaphosphorine-F, N-phenyl* | 6.96 | 95 | 20 | 1 | 77.0 | 5.11 |
| 10 | 1-Octene | 7.89 | *benzoxazaphosphorine-F, N-phenyl* | 6.96 | 105 | 20 | 1 | 79.8 | 3.15 |
| 11 | 1-Octene | 7.89 | *benzoxazaphosphorine-F, N-phenyl* | 6.96 | 95 | 20 | 1 | 82.3 | 4.16 |
| 12 | 1-Octene | 7.89 | *benzoxazaphosphorine-F, N-(t-Bu), di-t-Bu substituted* | 6.32 | 95 | 20 | 1 | 80.5 | 0.63 |

TABLE I-continued

Hydroformylation of 1-Octene

| | Olefin | Grams olefin | Ligand | Mmole ligand | T° C. | Rh, mg | H₂/CO ratio | % conv | N/I |
|---|---|---|---|---|---|---|---|---|---|
| 13 | 1-octene | 7.89 | *(amidofluorophosphite with N-CH(CH₃)Ph)* | 6.96 | 95 | 20 | 1 | 94.6 | 2.78 |
| 14 | 1-Octene | 7.89 | *(amidofluorophosphite with N-CH₂CH₂Ph)* | 11.64 | 95 | 20 | 1 | 86.0 | 12.8 |
| 15 | 1-Octene | 7.89 | *(amidofluorophosphite with N-CH₂CH₂Ph)* | 5.82 | 95 | 20 | 1 | 86.3 | 8.6 |
| 16 | 1-Octene | 7.89 | *(amidofluorophosphite with N-CH₂CH₂Ph)* | 2.91 | 95 | 20 | 1 | 86.7 | 4.8 |

Lines 1, 3, 4, 12, and 13 illustrate that various amidofluorophosphites can be used for the hydroformylation olefins.

Lines 4, 5, 6, and 7 show that as the concentration of the ligand is increased in the reaction mixture, the N/I ratio increases. Lines 14, 15, and 16 demonstrate this point with a different ligand and also show that variations in the ligand structure of the ligand have a strong influence on the outcome of the reaction.

A comparison on lines 6 and 8 shows that under otherwise similar conditions, changing the composition of the synthesis gas from an equimolar mixture to a 2:1 molar mixture causes the N/I ratio to increase.

A comparison on lines 9 and 10 shows that increasing the reaction temperature causes the N/I ratio to decrease.

Table II shows the results from hydroformylation runs with other olefins including substituted olefins.

TABLE II

Hydroformylation of Olefins

| | Olefin | Grams olefin | Ligand | Mmole ligand | T° C. | Rh, mg | H₂/CO ratio | % conv | N/I |
|---|---|---|---|---|---|---|---|---|---|
| 1 | 1-Tetradecene | 13.7 | *(amidofluorophosphite with N-Ph)* | 6.96 | 95 | 20 | 1 | 77.8 | 5.29 |
| 2 | Ethylhexyl methacrylate | 13.9 | *(amidofluorophosphite with N-Ph)* | 6.96 | 95 | 20 | 1 | 0 | NA |

TABLE II-continued

Hydroformylation of Olefins

| | Olefin | Grams olefin | Ligand | Mmole ligand | T° C. | Rh, mg | H₂/CO ratio | % conv | N/I |
|---|---|---|---|---|---|---|---|---|---|
| 3 | 1,7-Octadiene | 7.71 | (ligand) | 6.96 | 95 | 20 | 1 | 96.4 | 29.5% mono aldehydes 70.5% dialdehydes of which 66.3% is 1, 10 decanedial |
| 4 | Allyl alcohol | 5.0 | (ligand) | 6.96 | 95 | 20 | 1 | 0.0 | NA |
| 5 | Isobutyl vinyl ether | 7.0 | (ligand) | 6.96 | 95 | 20 | 1 | 46.0 | 1.16 |
| 6 | Vinyl Acetate | 6.02 | (ligand) | 6.96 | 95 | 20 | 1 | 100 | 0.067 (I/N = 14.8) |
| 7 | 2-butene, mixed | 21 | (ligand) | 6.96 | 95 | 20 | 1 | 30 | 0.79 |
| 8 | Butyl acrylate | 8.97 | (ligand) | 6.96 | 95 | 20 | 1 | 0 | NA |
| 9 | Cyclooctene | 7.71 | (ligand) | 6.96 | 95 | 20 | 1 | 0 | NA |
| 10 | Cyclooctene | 7.71 | (ligand) | 6.96 | 105 | 20 | 1 | 11.1 | NA |

TABLE II-continued

Hydroformylation of Olefins

| | Olefin | Grams olefin | Ligand | Mmole ligand | T° C. | Rh, mg | H₂/CO ratio | % conv | N/I |
|---|---|---|---|---|---|---|---|---|---|
| 11 | 1-Octene | 7.89 | (amido-fluorophosphite, N-Ph) | 6.96 | 95 | 20 | 1 | 82.4 | 5.58 |
| 12 | Cyclohexene | 5.75 | (amido-fluorophosphite, N-Ph) | 6.96 | 95 | 20 | 1 | 12 | NA |
| 13 | Cyclohexene | 5.75 | (amido-fluorophosphite, N-Ph) | 3.48 | 105 | 20 | 1 | 41.5 | NA |
| 14 | 4-Methyl styrene | 8.27 | (amido-fluorophosphite, N-CH(CH₃)Ph) | 6.96 | 95 | 20 | 1 | 99.6 | 0.70 |
| 15 | Methyl methacrylate | 7.01 | (amido-fluorophosphite, N-CH(CH₃)Ph) | 3.48 | 105 | 20 | 1 | 96.8 | N/I = 8.77; 92.9% selectivity to aldehydes, 7.1% to methyl isobutyrate |
| 16 | Ethylene | 1.97 | (amido-fluorophosphite, N-Ph) | 6.96 | 95 | 20 | 1 | 98.2 | NA |

Line 1 demonstrates that these catalysts work well with heavier olefins as 1-tetradecene was cleanly converted to pentadecanal.

Line 3 demonstrates that non conjugated diolefins can be hydroformylated using the amido-fluorophosphite catalysts.

Lines 5 and 6 demonstrate that oxygen substituted olefins are suitable for use with this class of hydroformylation catalysts.

Line 7 shows that mixed 2-butenes will react but at a slower rate than α-olefins.

Line 2 shows that allyl alcohol is not a suitable olefin for this particular ligand.

Lines 2, 8, and 15 show that unsaturated ester compounds are less reactive but if suitable conditions are chosen (line 15), these compounds are reactive with amido-fluorophosphite ligands.

Lines 9, 10, 12, and 13 show that internal olefins may require higher temperatures and longer reaction times to achieve good conversion to aldehyde products.

Line 16 shows that the process works well for ethylene.

Bench Unit Hydroformylation of Propylene

A catalyst solution was prepared under nitrogen using a charge of 20 mg of rhodium (0.194 mmol, as rhodium dicarbonyl acetonyl acetate), various amounts of the ligand as indicated in Table III; and 190 ml of Texanol™ Isobutyrate (2,2,4-trimethylpentane-1,3-diol diisobutyrate). The mixture was stirred under nitrogen until a homogeneous solution was obtained (heated if necessary).

The mixture was charged to the reactor in a manner described previously and the reactor sealed. The reactor pressure control was set at 17.9 bar (260 psig), and the external oil jacket on the reactor was heated to 85° C. Hydrogen, carbon monoxide, nitrogen, and propylene vapors were fed through the frit at the base of the reactor, and the reactor was allowed to build pressure. The hydrogen and carbon monoxide ($H_2$/CO ratio was set to be 1:1 or other desired ratio) were fed to the reactor at a rate of 6.8 liters/min and the nitrogen feed was set at 1.0 liter/min. The propylene was metered as a liquid and fed at a rate of 1.89 liters/min (212 grams/hour). The temperature of the external oil was modified to maintain an internal reactor temperature of 95° C. The unit was usually operated for 3 to 5 hours and hourly samples taken. The hourly samples were analyzed as described above using a standard GC method. The last two to three samples of the run were used to determine the N/I ratio and catalyst activity. The foregoing procedures were conducted for the ligand listed below.

TABLE III

Hydroformylation of Propylene in the Continuous Bench Unit

| Run # | Ligand | $H_2$/CO Ratio | Ligand/Rh Ratio (mmole ligand) | Activity* | N/I Ratio of $C_4$ Aldehyde | Comments |
|---|---|---|---|---|---|---|
| 1 | 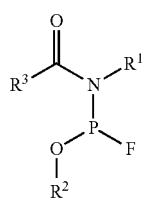 | 1.0 | 53:1 (3.99 mmole) | 2.92 | 1.60 | Last 2 h of 3 h run with declining activity. Rh 2-ethylhexanoate as Rh source. |
| 2 | (same as above) | 2.0 | 53:1 (3.99 mmole) | 2.55 | 1.59 | 2nd hour of 2 h run with declining activity. Rh 2-ethylhexanoate as Rh source. |
| 3 | (same as above) | 1.0 | 20.6 (3.99 mmole) | 0.67 | 1.50 | Last 3 h of 4 h run with declining activity. Rh dicarbonyl Acac as Rh source. |
| 4 | (same as above) | 1.0 | 77.2 (15.0 mmole) | 0.42 | 2.18 | Last 3 h of 5 h run with declining activity. Rh dicarbonyl Acac as Rh source. |

All runs were made at 260 psig, 95° C., syn gas at 6.8 L/min, $C_3H_6$ at 212 g/h, and N2 at 1.0 L/h. Runs 1 and 2 used 7.7 milligrams of Rh. Runs 3 and 4 used 20 milligrams of Rh. Activity is measured as kilograms of aldehyde per gram of Rh-hour.

The invention has been described in detail with particular reference to preferred embodiments thereof, but it will be understood that variations and modifications will be effected within the spirit and scope of the invention.

I claim:

1. A ligand of a catalyst composition having the general structure (I):

(I)

wherein $R^1$, $R^2$, and $R^3$ are hydrocarbyl groups which contain a total of up to about 70 carbon atoms, wherein the hydrocarbyl group represented by $R^1$, $R^2$, and $R^3$ are the same or different and are selected from the group consisting of an alkyl group, a cycloalkyl group and an aryl group containing a total of up to about 40 carbon atoms, and wherein $R^2$ and $R^3$ in combination or collectively represent a divalent hydrocarbylene group containing up to about 40 carbons.

2. The ligand according to claim 1, wherein the total carbon content of substituents $R^1$, $R^2$, and $R^3$ is in the range of about 3 to 40 carbon atoms.

3. The ligand according to claim 1, wherein the alkyl group is selected from the group consisting of methyl, ethyl, butyl, pentyl, hexyl, 2-ethylhexyl, octyl, decyl, dodecyl, octadecyl and isomers thereof.

4. The ligand according to claim 1, wherein the cycloalkyl group is selected from the group consisting of cyclopentyl, cyclohexyl and cycloheptyl.

5. The ligand according to claim 1, wherein the aryl group is selected from the following:

(II)

-continued

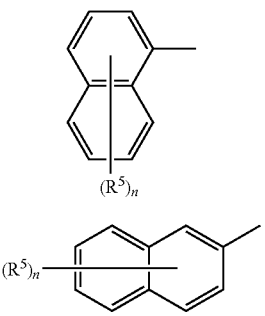

wherein $R^4$ and $R^5$ are one or more substituents independently selected from the group consisting of alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, and sulfonate salts.

6. The ligand according to claim 1, wherein the divalent group is selected from the group consisting of an alkylene, a cyclohexylene and an arylene.

7. The ligand according to claim 1, wherein the compound is an amido-fluorophosphite ester wherein the amido-fluorophosphite ester oxygen atom is bonded directly to a ring carbon atom of a carbocyclic, aromatic group.

8. A catalyst comprising:
i. at least one amido-fluorophosphite ester ligand having the general structure (I)

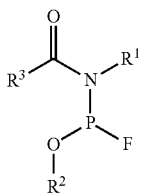

wherein $R^1$, $R^2$, and $R^3$ are hydrocarbyl groups which contain a total of up to about 70 carbon atoms,
ii. at least one transition metal; and
iii. a solvent wherein the hydrocarbyl group represented by $R^1$, $R^2$, and $R^3$ are the same or different and are selected from the group consisting of an alkyl group, a cycloalkyl group and an aryl group containing a total of up to about 40 carbon atoms, and
wherein $R^2$ and $R^3$ in combination or collectively represent a divalent hydrocarbylene group containing up to about 40 carbons.

9. The catalyst according to claim 8, wherein the transition metal is a Group VIII metal.

10. The catalyst according to claim 9, wherein the transition metal is rhodium.

11. The catalyst according to claim 9, wherein the ratio of gram moles amido-fluorophosphite ester ligand to gram atoms transition metal is from about 1:1 to about 300:1.

12. A process for preparing an amido-fluorophosphite ester ligand according to claim 1 comprising contacting an amido-chlorophosphite and a fluoride containing compound in a solvent to produce the amido-fluorophosphite compound.

13. The process according to claim 12, wherein the fluoride containing compound is selected from the group consisting of anhydrous hydrogen fluoride, hydrogen fluoride-pyridine complex, potassium fluoride, ammonium fluoride, antimony trifluoride in combination with triethyl amine, and cesium fluoride.

14. A process for the production of an aldehyde comprising contacting hydrogen, carbon monoxide, and an olefin in the presence of a catalyst comprising:
i. at least one amido-fluorophosphite ester ligand having the general structure (I):

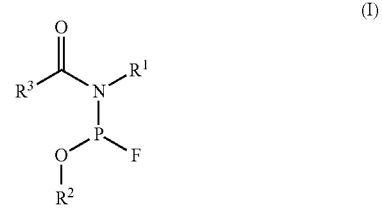

wherein $R^1$, $R^2$, and $R^3$ are hydrocarbyl group which contain a total of up to about 70 carbon atoms,
ii. at least one transition metal, and
iii. a solvent wherein the hydrocarbyl group represented by $R^1$, $R^2$, and $R^3$ are the same or different and are selected from the group consisting of an alkyl group, a cycloalkyl group and an aryl group containing a total of up to about 40 carbon atoms, and
wherein $R^2$ and $R^3$ in combination or collectively represent a divalent hydrocarbylene group containing up to about 40 carbons.

15. The method according to claim 14, wherein the transition metal is a Group VIII metal.

16. The method according to claim 15, wherein the transition metal is rhodium.

17. The method according to claim 14, wherein the hydrogen and carbon monoxide are provided as synthesis gas.

18. The method according to claim 16, wherein the ratio of gram moles amido-fluorophosphite ligand to gram atoms transition metal is at least 1:1.

* * * * *